United States Patent
Skiffington et al.

(10) Patent No.: US 10,407,654 B1
(45) Date of Patent: *Sep. 10, 2019

(54) GROWTH PLATE DEVICES, KITS AND ASSEMBLIES

(71) Applicant: Charm Sciences, Inc., Lawrence, MA (US)

(72) Inventors: Richard T. Skiffington, North Reading, MA (US); Stanley E. Charm, Boston, MA (US); Bryan A. Roberts, Ashland, MA (US)

(73) Assignee: Charm Sciences, Inc., Lawrence, MA (US)

( * ) Notice: Subject to any disclaimer, the term of this patent is extended or adjusted under 35 U.S.C. 154(b) by 259 days.

This patent is subject to a terminal disclaimer.

(21) Appl. No.: 14/665,560

(22) Filed: Mar. 23, 2015

Related U.S. Application Data

(60) Provisional application No. 62/079,926, filed on Nov. 14, 2014, provisional application No. 61/968,442, filed on Mar. 21, 2014.

(51) Int. Cl.
  *C12M 1/00* (2006.01)
  *C12M 1/32* (2006.01)
  *C12M 1/34* (2006.01)
  *C12M 3/00* (2006.01)

(52) U.S. Cl.
  CPC ............ *C12M 23/12* (2013.01); *C12M 23/38* (2013.01); *C12M 23/44* (2013.01); *C12M 23/46* (2013.01); *C12M 41/36* (2013.01)

(58) Field of Classification Search
  CPC ...... C12M 23/12; C12M 23/38; C12M 23/44; C12M 23/46; C12M 41/36
  USPC ................ 435/288.3, 289.1, 305.1
  See application file for complete search history.

(56) References Cited

U.S. PATENT DOCUMENTS

| | | | | |
|---|---|---|---|---|
| 4,440,301 A | * | 4/1984 | Intengan ................ | B01L 3/508 206/456 |
| 5,080,869 A | * | 1/1992 | McCormick ........... | G01N 1/312 422/500 |
| 5,096,676 A | * | 3/1992 | McPherson ............... | C30B 7/00 117/206 |
| 5,661,029 A | * | 8/1997 | Self ........................ | G02B 21/34 359/398 |
| 5,694,478 A | | 12/1997 | Braier et al. .................. | 382/133 |
| 6,243,486 B1 | | 6/2001 | Weiss ............................ | 382/133 |
| 6,265,203 B1 | | 7/2001 | Ushiyama .................. | 435/253.6 |
| 6,381,353 B1 | | 4/2002 | Weiss ............................ | 382/133 |

(Continued)

FOREIGN PATENT DOCUMENTS

| WO | WO 95/14452 | 6/1995 | ............. A61F 13/15 |
|---|---|---|---|
| WO | WO 2012/092181 | 7/2012 | ................ C12Q 1/04 |
| WO | W/2012/176751 | 12/2012 | ............ C12M 1/100 |

*Primary Examiner* — Liban M Hassan
(74) *Attorney, Agent, or Firm* — MacCord Mason PLLC

(57) ABSTRACT

Culture medium devices and systems are shown and described. In one embodiment a growth plate includes an upper surface, a recessed well, a raised platform having an opposing cavity, and raised extensions having an opposing receiving aperture. Typically, the well is recessed below the top surface and the platform is above the upper surface. A growth plate assembly typically includes at least a first growth plate's raised stacking surfaces being temporarily received by a second growth plate's receiving surfaces, thereby temporarily securing growth plates together.

14 Claims, 10 Drawing Sheets

(56) References Cited

U.S. PATENT DOCUMENTS

| | | | |
|---|---|---|---|
| 6,446,807 B1 * | 9/2002 | Lafond | B65D 21/0228 206/456 |
| 6,756,225 B2 | 7/2004 | Bedingham et al. | 435/305.1 |
| 7,298,885 B2 | 11/2007 | Green et al. | 382/133 |
| 7,298,886 B2 | 11/2007 | Plumb et al. | 382/33 |
| 7,319,031 B2 | 1/2008 | Vent et al. | 435/286.2 |
| 7,351,574 B2 | 4/2008 | Vent | 435/286.2 |
| 7,452,711 B2 * | 11/2008 | Daykin | C12M 23/38 435/288.3 |
| 7,496,225 B2 | 2/2009 | Graessle et al. | 382/133 |
| 7,738,689 B2 | 6/2010 | Plumb et al. | 382/133 |
| 7,865,008 B2 | 1/2011 | Graessle et al. | 382/133 |
| 7,901,933 B2 | 3/2011 | Green et al. | 435/287.9 |
| 7,957,575 B2 | 6/2011 | Plumb et al. | 382/133 |
| 8,094,916 B2 | 1/2012 | Graessle et al. | 382/133 |
| 8,260,026 B2 | 9/2012 | Plumb et al. | 382/133 |
| 8,417,014 B2 | 4/2013 | Bolea | 382/133 |
| 8,579,080 B2 | 11/2013 | Angelico | 435/287.3 |
| 8,588,505 B2 | 11/2013 | Bolea | 382/133 |
| 2005/0142033 A1 * | 6/2005 | Glezer | B01L 3/5085 422/400 |
| 2005/0239200 A1 | 10/2005 | beckwith et al. | 435/299.1 |
| 2006/0166305 A1 | 7/2006 | Jiang et al. | 435/29 |
| 2008/0286839 A1 * | 11/2008 | Hsu | A61K 8/0212 435/104 |
| 2009/0141345 A1 | 6/2009 | Tsuchiya | 359/393 |
| 2010/0273260 A1 | 10/2010 | Odane et al. | 435/396 |
| 2012/0121543 A1 | 5/2012 | Teather et al. | 424/93.2 |

\* cited by examiner

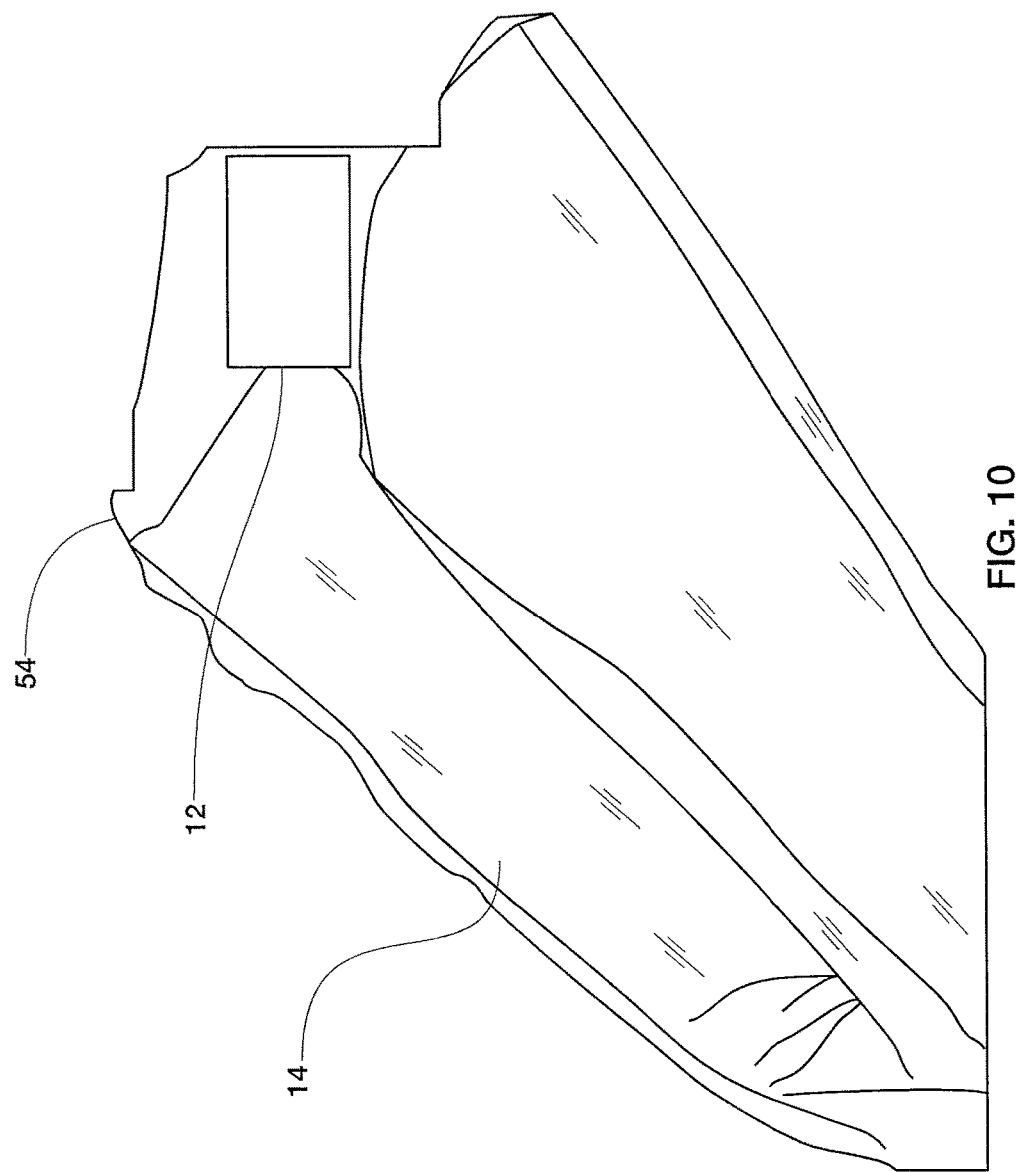

GROWTH PLATE DEVICES, KITS AND ASSEMBLIES

This application claims the benefit of U.S. provisional application No. 61/968,442, filed Mar. 21, 2014, and U.S. provisional application No. 62/079,926, filed Nov. 14, 2014, both of which are incorporated by reference.

FIELD OF THE TECHNOLOGY

The present disclosure relates generally to culture testing, and more particularly to improved growth plate devices, kits, and methods.

BACKGROUND

It is desirable to provide rapid, effective detection and identification of various and numerous microorganisms in test samples, such as samples of water, food, such as milk, and body fluids. Microorganisms of interest include all aerobic bacteria and specific bacterial groups, such as coliforms. Other microorganisms of interest include a variety of molds, allergens, and any other pathogens or the like.

Classical methods for culturing various microorganisms for detection and identification thereof often include the use of growth plates. However, preserving the integrity and usefulness of growth plates during shipment, storage and manipulation presents demanding concerns. Further, the use of conventional growth plates often requires skilled technicians. Conventional systems to support growth plate testing are bulky, unreliable and often require too large of a footprint in a laboratory and are too expensive. And particularly in the food industry, where testing is very cost-sensitive, the reliability and efficiency of growth plate testing should be user-friendly and inexpensive, without sacrificing accuracy.

Therefore, Applicants desire alternative cost-effective, user-friendly growth plate devices, kits and methods that are useful and maintain the integrity of the units in a variety of set-ups for accurate testing.

SUMMARY

In accordance with the present disclosure, growth plate devices and methods are provided for packaging, storing, organizing, and testing culture growth plates and the like. This disclosure provides improved growth plate devices, kits, assemblies and methods that are convenient, efficient, and safe for the user.

One embodiment of the disclosure is a growth plate having a recessed well, a pair of opposing proximate extensions, and a distal raised platform. Typically, the plate has an upper face having a front portion, a rear portion, and a side periphery. The pair of opposing proximate extensions are typically adjacent to the recessed well, and at least one of the proximate extensions comprises an underside receiving aperture. The distal raised platform is typically adjacent to the recessed well. The recessed well is positioned between the raised platform and the proximate extensions.

In particular examples, the recessed well is aligned below and parallel to the distal raised platform. The distal raised platform may span substantially a length of a diameter of the recessed well.

In certain examples, the front portion includes a handling opening between the proximate extensions. Further, the plate may include a pair of support ends opposing the handling opening.

In some examples, the stacking surfaces include tapered edges adapted to guide corresponding adjoining raised stacking surfaces and the receiving aperture in an assembled position. The recessed well may be aligned below and parallel to an upper face of the plate and includes a grid. In certain examples, the recessed well includes a molded, printed, or the like grid visible for colony counting. Further, the growth plate may be a peel plate having at least one removable peel layer adapted to temporarily enclose the recessed well and at least a portion of the upper face. The peel layer may further include a peel tab that is generally removably secured to a front end of the plate. For instance, the removable peel layer may include a self-wicking adhesive periphery adapted to removably adhere to the upper face of the plate.

Another embodiment of the disclosure is a growth plate assembly having a plurality of growth plates. The growth plates may include a recessed well protruding below an upper face; a raised platform on a first end of the plate adjacent to the recessed well, the raised platform having an underside cavity; and a pair of opposing proximate extensions extending from a second end of the plate, each of the proximate extensions having an underside receiving aperture. Typically, a first growth plate's raised platform and proximate extensions may be received by a second growth plate's corresponding platform cavity and receiving aperture in an aligned position. Thus the first growth plate may be removably secured about the second growth plate.

In certain examples, the assembly may be substantially stable to support about fifty aligned growth plates, for instance above a solid surface. Each of the growth plates may include a handling opening indented toward the recessed well. Further, the assembly may include a column of the aligned handling openings.

In some examples, the recessed well is aligned below and parallel to the distal raised platform. The raised platform may include a width adapted to support a user's finger. Each of the growth plates may be sterilized and including a removable peel layer. Further, the removable peel layer includes a peel tab.

Yet another embodiment of the disclosure is a growth plate having a recessed well having a sunken wall protruding from an upper face; a pair of opposing proximate extensions adjacent the recessed well, wherein each of the proximate extensions having an underside receiving aperture; a handling opening between the proximate extensions having a peel tab of a removable peel layer aligned on the handling opening; and a distal raised platform adjacent the recessed well, wherein the raised platform having an underside cavity.

A further embodiment of the disclosure is an assembly for enumerating a microorganism having a recessed well, a raised platform, a dried media culture disc, and a removable cover. Typically, the recessed well receives a sample and the raised platform is adjacent to the recessed well. The dried media culture disc is typically positioned within the recessed well. The removable cover typically includes a first end fixedly secured adjacent to the raised platform, while the opposing second removable end removably encloses the recessed well.

In some examples, the cover's second end includes a peel tab. Further, the removable cover may include an adhesive periphery, for instance on three sides, to removably adhere to an upper face of the plate. The recessed well may be aligned below and parallel to an upper face of the plate. The recessed well may include a grid that is generally visible on the upper face surface and/or lower face surface, for instance for colony counting after the sample has absorbed and diffused throughout the dried media culture disc.

In certain examples, the dried media culture disc supports at least one of (a) an adhesive, (b) a gelling agent, (c) a bacterial nutritive ingredient, (d) a fibrous material, (e) a percent liquid organic solvent, and (f) a cellulosic material. In addition, the plate may include an access indent that is generally opposite the raised platform. The plate may have proximate extensions on opposing sides of the access indent, and the extensions may include an alignment tab.

Another embodiment of the disclosure is a peel plate having a recessed well, a pair of opposing proximate extensions, and a distal raised platform. Typically, the recessed well is spaced between the distal raised platform and the proximate extensions. The recessed well typically has a sunken wall protruding from an upper face. The pair of opposing proximate extensions are typically adjacent to the recessed well, and at least one of the proximate extensions include a proximate tab. The distal raised platform is typically adjacent to the recessed well.

In certain examples, a removable cover encloses the recessed well. The cover may include a peel tab, for instance which is removably secured to a proximate end of the plate. Further, the cover may include a self-wicking adhesive periphery removably adhering to an upper face of the plate. The recessed well may be aligned below and parallel to an upper face of the plate and includes a printed grid. In particular examples, the printed grid is visible on the upper face surface and/or lower face surface, for instance for colony counting after the sample has absorbed and diffused. The proximate extensions may be spaced between an access indent. The proximate extensions may each include a rounded corner entry to the access indent. A removable cover may have a peel tab that is generally aligned along the access indent.

In some examples the distal raised platform spans a length of a diameter of the recessed well. Further, a top perimeter may span around the distal raised platform. The distal platform may include a raised edge extending the platform above the top perimeter.

In particular examples, a culture medium is positioned, i.e. secured or the like, in the recessed well. The culture medium may be a dried media culture disc. The dried media culture disc may comprise a bacterial nutritive ingredient. The dried media culture disc may comprise a growth indicator color-developing agent. For instance, the color-developing agent may be triphenyltetrazolium chloride, 3-(p-iodophenyl)-2-(p-nitrophenyl)-5-phenyl-2H-tetrazolium chloride, 3-(4,5-dimethyl-2-thiazolyl)-2,5-diphenyl-2H-tetrazolium bromide, 5-bromo-3-indolyl-beta.-D-galactoside, bromothymol blue, and neutral red. Further, the dried media culture disc may comprise a plate count agar or plate count agar individual components. In addition, the dried media culture disc may comprise a yeast and mold growth media. The dried media culture disc may comprise a bacterial nutritive ingredient selective medium for growth of indicator organisms. For example, the bacterial nutritive ingredient may comprise selective growth agents for coliform, *E. coli*, enterbacteriaceae, or pathogens. In addition, the bacterial nutritive ingredient may comprise selective growth agents for *salmonella, listeria*, or camphlobacter.

In some examples, the dried media culture disc comprises an organic solvent. For instance, the organic solvent may comprise a C1-C5 alcohol. In addition, the organic solvent may comprise 2-propanol. The dried media culture disc may comprise an enhancer. Further, the dried media culture disc may comprise a selective agent.

In particular examples, the sample is a liquid sample. For instance, the liquid sample is a liquid extract selected from the group consisting of a solid, a partial solid, and a combination thereof.

In another embodiment of the disclosure, a peel plate includes a recessed well protruding below an upper face; a raised platform that is adjacent the recessed well and extends in an opposing direction from the recessed well; and an adhesive cover removably enclosing the recessed well.

In certain examples the recessed well includes a printed grid. For instance, the printed grid may include a plurality of vertical lines and a plurality of intersecting horizontal lines.

In some examples, the raised platform is positioned on a distal portion of the plate and spans a length of a diameter of the recessed well. Further, the raised platform may include a width to support at least one user's finger, or the like. The raised platform may include a raised edge extending away from the upper face. The plate typically includes a top perimeter around the raised platform. The adhesive cover may include a peel tab removably secured to a proximate end of the plate. An access indent may be aligned opposite the raised platform. The access indent may be positioned between opposing proximate extensions. The proximate extensions may include a proximate tab aligning multiple plates in a layered and/or stacked positioned. Typically, the proximate extensions include a rounded corner entry to the access indent.

Yet another embodiment is a method for enumerating microorganisms on a peel plate having a recessed well, a raised platform, a media culture, and an adhesive cover having a tab. The method typically includes at least one of the following: applying pressure with a user's fingers against the raised platform; lifting the tab vertically upward, thereby exposing the recessed well and maintaining coverage of at least a portion of the cover to the plate; dispensing a sample on the media culture; reapplying the adhesive cover to enclose the recessed well; incubating the peel plate; and enumerating the microorganisms, when present, on the media culture.

Further embodiments include a growth plate having a top surface, a recessed well, and a raised stacking surface with an opposing receiving aperture. The top surface may have a front portion, a rear portion, and a side periphery. The recessed well is generally recessed, including sunken or the like, below the top surface and includes a bottom face. Typically, a first, second, third, and fourth raised stacking surface are aligned at corners of the top surface and extend above the top surface. Each of the raised stacking surfaces include an opposing receiving aperture.

In some examples, the recessed well includes a printed grid visible for colony counting. The growth plate may be a peel plate having at least one removable peel layer. The growth plate may be comprised of a material sufficient to withstand incubation temperatures. The growth plate may be comprised a material sufficient to withstand autoclave temperatures. Another embodiment of the disclosure is a growth plate with a top surface having a front portion, a rear portion, and a side periphery; at least one recessed well recessed below the top surface; and a plurality of raised stacking surfaces extending above the top surface and including an opposing receiving aperture.

In some examples, the front portion includes a handling opening that is generally indented toward the recessed well. The plate may further include a pair of support ends on opposing sides of the handling opening. The plate may include four raised stacking surfaces, for instance which are aligned at corners of the top surface. The raised stacking surfaces may include tapered edges to guide temporarily adjoining raised stacking surfaces and the receiving apertures. The recessed well may include a printed grid that is generally visible for colony counting. The printed grid may include grid lines chosen from vertical lines, horizontal lines, the like, and a combination thereof. The growth plate may be a peel plate having at least one removable peel layer, but including two or more layers. The growth plate may be comprised of a material sufficient to withstand incubation temperatures. In addition, the growth plate may be comprised of material sufficient to withstand autoclave temperatures.

In yet another embodiment, a growth plate assembly includes a plurality of growth plates that are configured to be temporarily stacked and thereby spaced parallel about one another. The assembly may include growth plates having a top surface, at least one recessed well recessed below the top surface, and a plurality of raised stacking surfaces extending above the top surface and including an opposing receiving aperture. Typically, a first growth plate's raised stacking surfaces is temporarily received by a second growth plate's receiving apertures, thereby the first growth plate is spaced substantially parallel about the second growth plate.

In some examples, the assembly is substantially stable to support a variety of configurations, including, but not limited to, about fifty aligned growth plates. Each of the growth plates may include a handling opening that is generally indented toward the recessed well. For instance, the assembly may include a column of the aligned handling openings. Further, each of the growth plates may include four raised stacking surfaces that are generally aligned at corners of the top surfaces.

The above summary was intended to summarize certain embodiments of the present disclosure. Embodiments will be set forth in more detail in the figures and description of embodiments below. It will be apparent, however, that the description of embodiments is not intended to limit the present inventions, the scope of which should be properly determined by the appended claims.

BRIEF DESCRIPTION OF THE DRAWINGS

Embodiments of the disclosure will be better understood by a reading of the Description of Embodiments along with a review of the drawings, in which:

FIG. 10 is a side perspective view of one embodiment of elements of a growth plate packaging kit.

DESCRIPTION OF EMBODIMENTS

Figure 1:
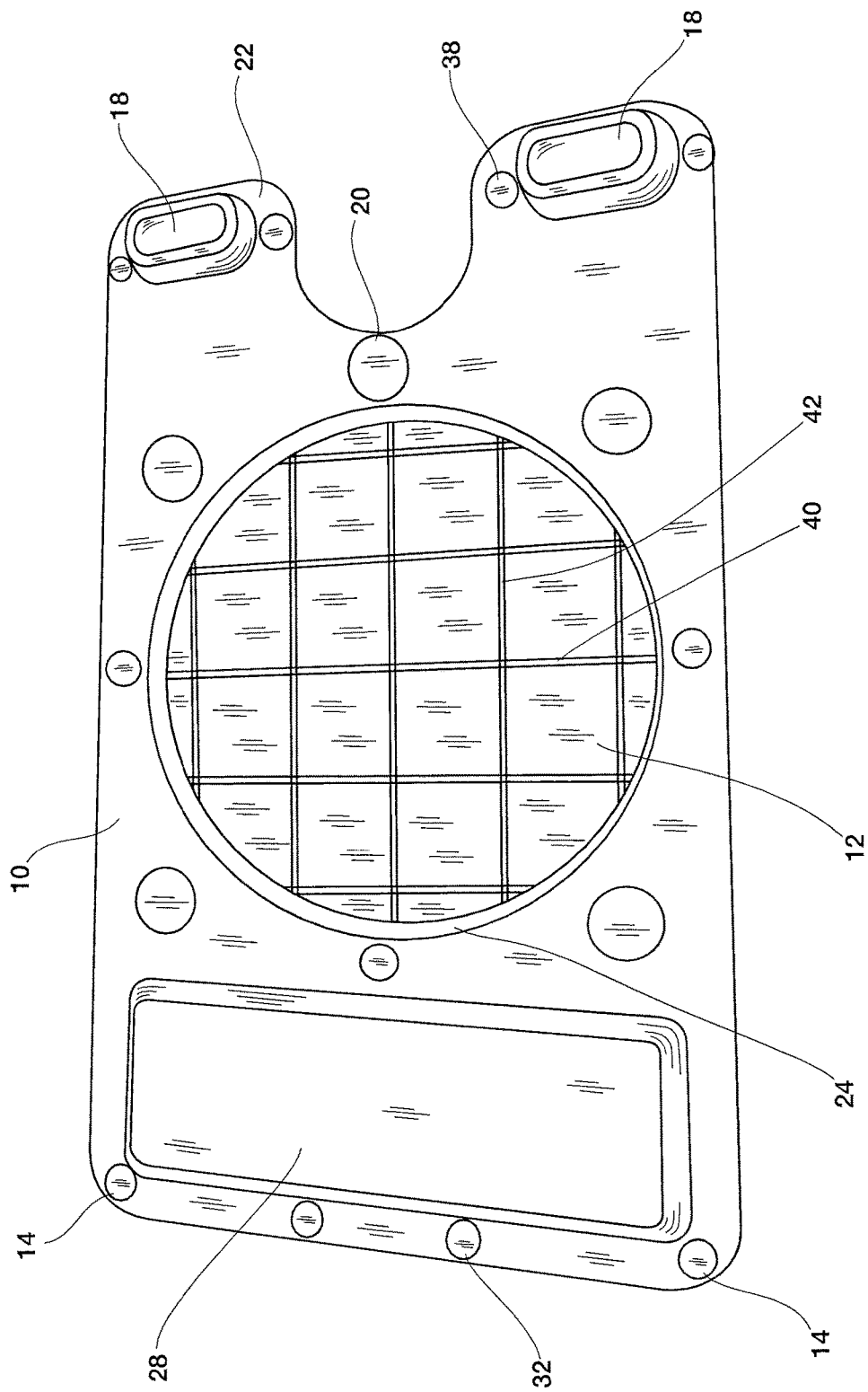
FIG. 1 is a top perspective view of one embodiment of an improved culture peel plate according to the disclosure.

In the following description, like reference characters designate like or corresponding parts throughout the several views. Also in the following description, it is to be understood that such terms as "forward," "rearward," "left," "right," "upwardly," "downwardly," and the like are words of convenience and are not to be construed as limiting terms.

Referring now to the drawings in general and FIG. 1 in particular, it will be understood that the illustrations are for the purpose of describing embodiments of the disclosure and are not intended to limit the disclosure or any invention thereto.

FIG. 1 introduces one example of a culture device peel plate 10 for enumerating and/or detecting a microorganism from a sample. The peel plate 10 is a semi-rigid waterproof plate onto which sample may be applied to enumerate microorganisms and the like. As seen in FIG. 1, one example of the peel plate 10 includes a recessed well 12, a distal raised platform 28, and opposing proximate tabs 22 having proximate extensions 28 to support stacked plates as shown and described herein. The upper face 14 of the plate typically has a top periphery 32 around the raised platform. The recessed well 12 includes a sunken wall 24 below the upper face 14. As shown in FIG. 1, the recessed well may include a grid, for instance having vertical line 40 and intersecting horizontal line 42 components useful for colony counting. In particular examples, the grid is molded, printed, and the like on the rear surface. The grid may be printed in a variety of ways, including inkjet printing, pad printing and the like. Regardless of the grid type, the grid is typically visible through the generally transparent culture device to the front surface and/or rear surface. The plate 10 is also typically transparent material so as to enable observation from the outside, including any of the printed grids shown and described herein.

FIG. 1 further shows the proximate end of the peel plate 10 includes an access indent 20 with opposing proximate tabs 22 between rounded corners 38. Typically, the proximate tabs 22 offset the proximate extensions, and the like, from the body of the plate, i.e. the well and the majority of the upper surface. Thereby the proximate tabs include proximate extensions 18 for alignment, stability, and support during testing/usage, including, but not limited to, layering and stacking plates in any of the arrangements and orientations shown and described.

Figure 2:
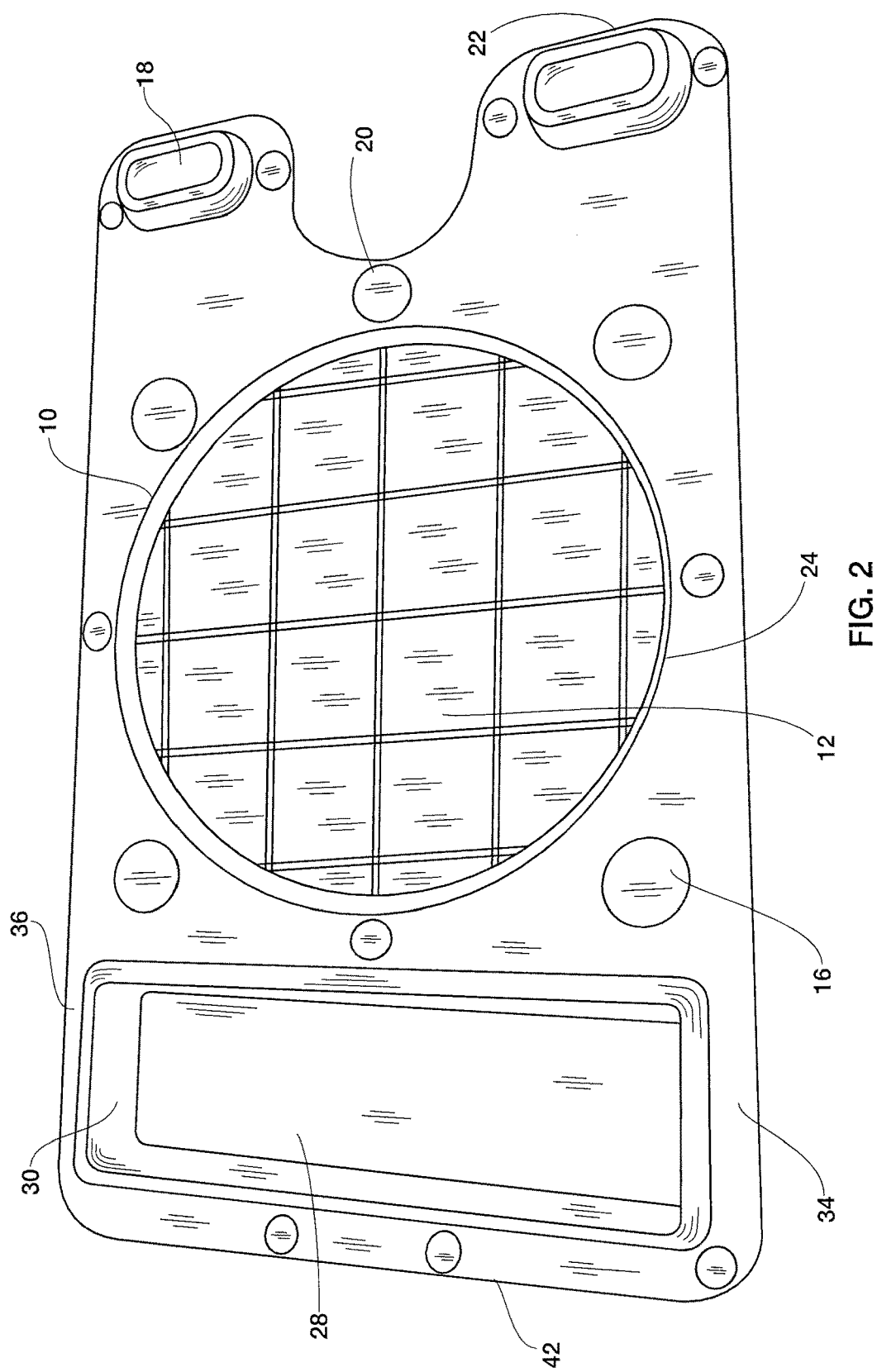
FIG. 2 is a bottom perspective view of the culture plate introduced in FIG. 1.
Figure 3:
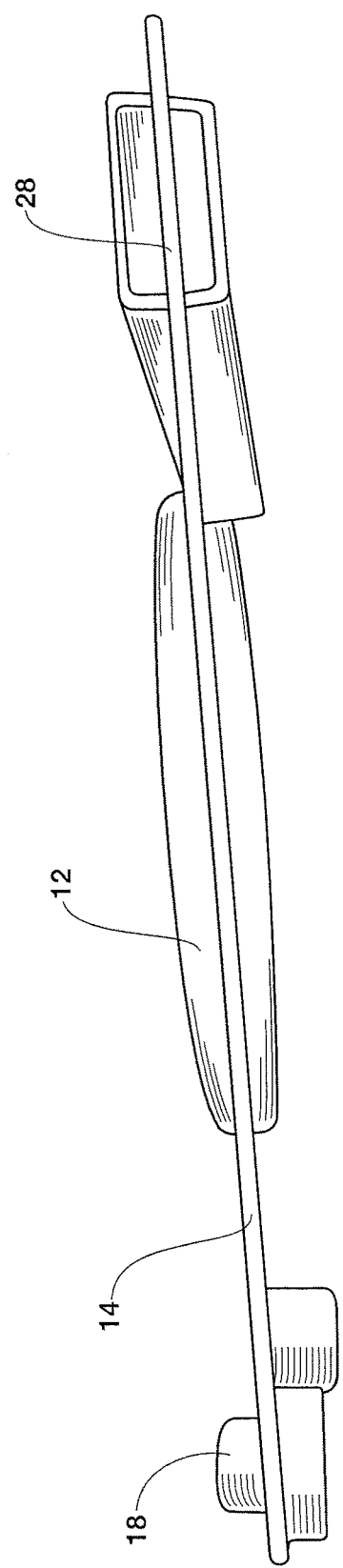
FIG. 3 is a side perspective view of the culture plate introduced in FIG. 1.

FIGS. 2 and 3 show a bottom and side view, respectively, of one example of a peel plate 10 having a raised edge 30 extending above the lower face 16 to define the raised platform 28. Typically, the peel plate has a distal thickness 42 to support any of the elements and testing procedures shown and described herein.

Figure 4:
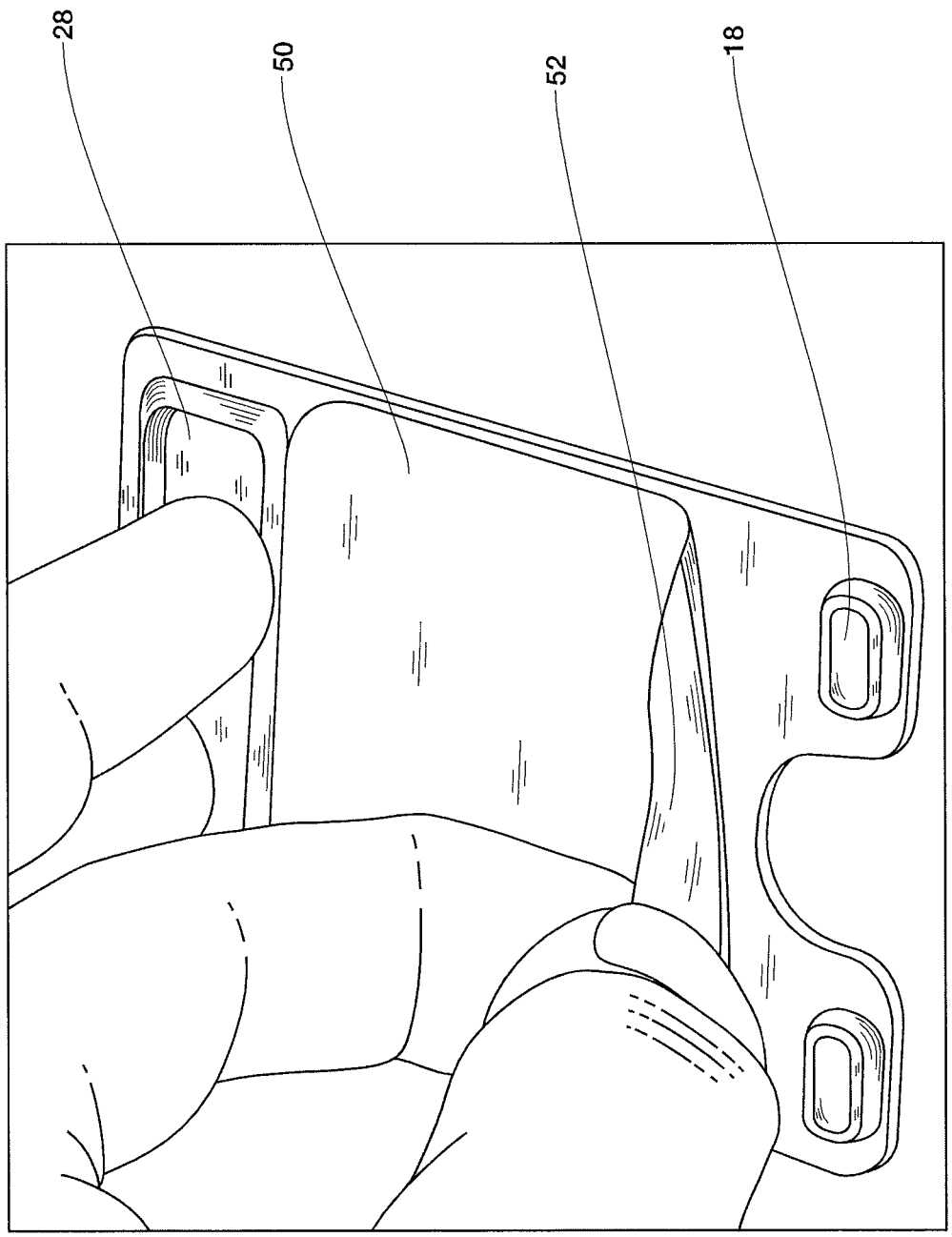
FIG. 4 is a side perspective view of the culture plate introduced in FIG. 1 with a peel tab.

FIG. 4 introduces one example of a peel plate 10 having a covered surface as shown and described herein. For instance, the peel plate 10 may be placed on a substantially level surface. The peel tab 52 may be lifted concurrently while pressure is applied to the raised platform 28 with the user's fingers, or the like. In particular examples, the tab 52 may be lifted vertically upwards and away to expose any of the culture medias shown and incorporated herein. In particular the culture media is any of the dried media culture disc shown and described herein.

Figure 5:
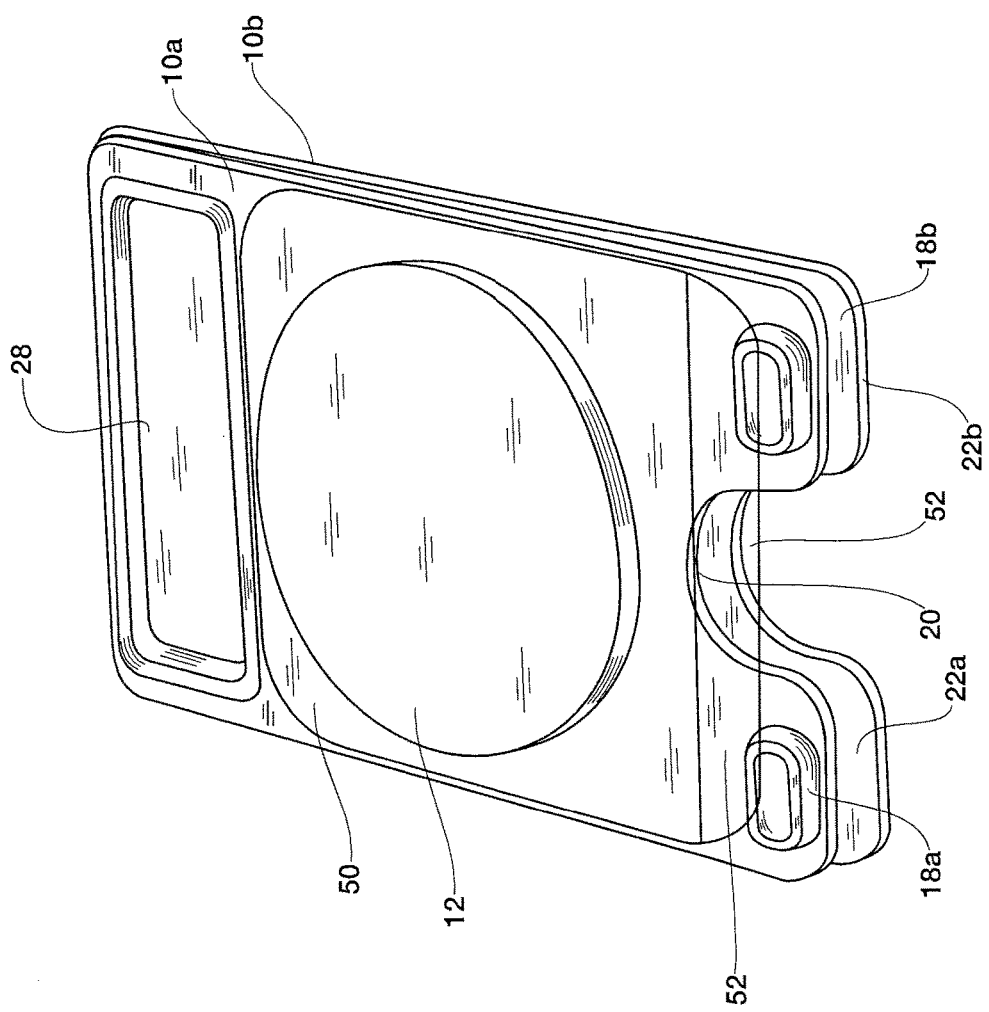
FIG. 5 is a top perspective view of one embodiment of an assembly of a plurality of stacked culture plates according to the disclosure.

FIG. 5 illustrates one example of layered, or otherwise stacked, peel plates 10a, 10b as shown and described herein.

The stacked arrangement may be incubated as understood by those skilled in the art having the benefit of this disclosure. For instance, the stacked plates may be incubated with their respective adhesive covers 50 down and grid sides aligning upward. Applicants have unexpectedly discovered the plates may be stacked by aligning two pillars and the rectangular platform without affecting plate heat transfer, for instance due to the spacing between plates offset by the corresponding stacking surfaces.

Figure 6:
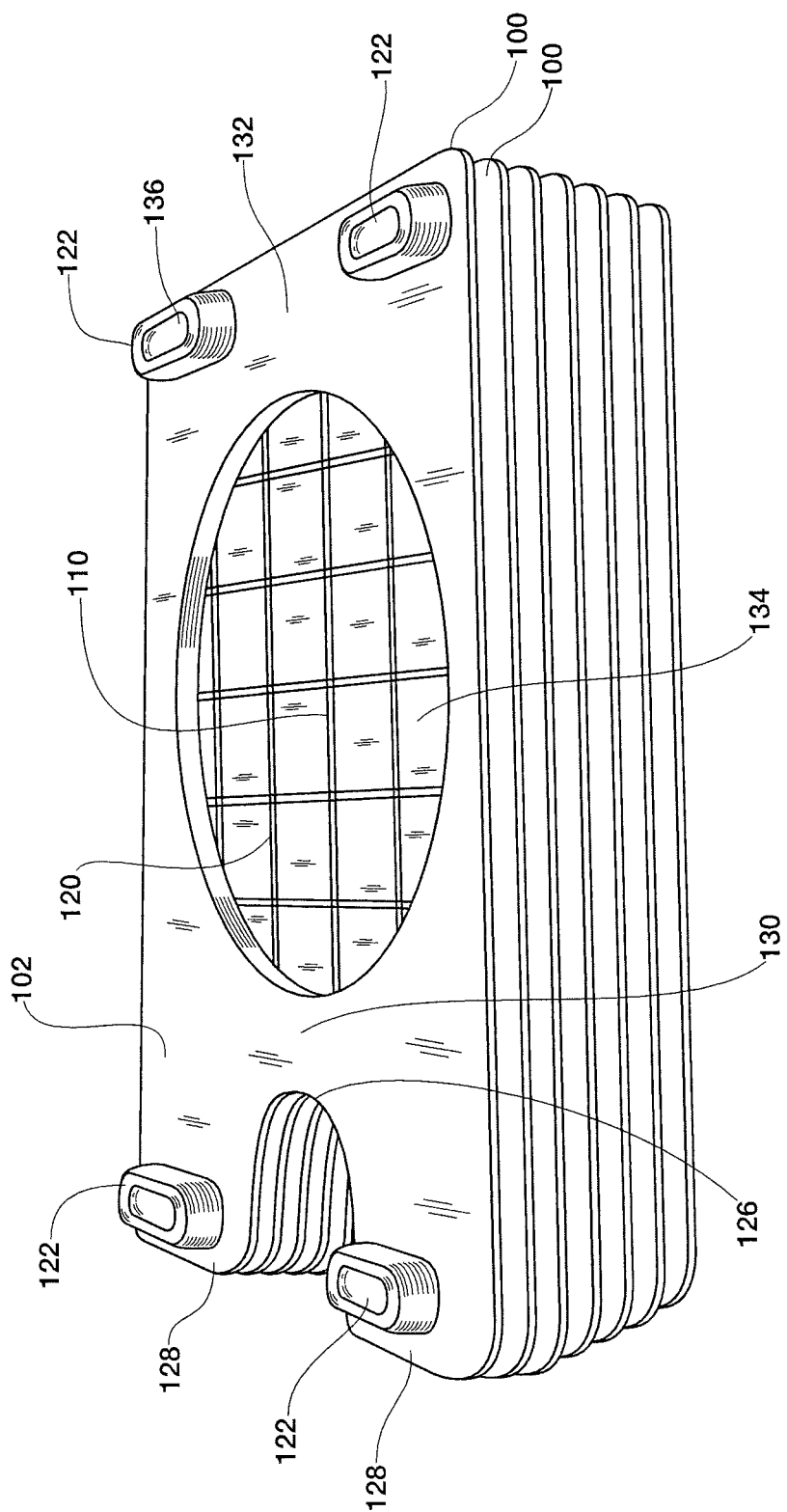
FIG. 6 is a font perspective view of an alternative embodiment of a growth plate assembly according to the disclosure.

FIG. 6 illustrates one alternative example of a growth plate assembly, which includes several growth plates 100 to provide stability with a minimum footprint. The minimum footprint is advantageous on a variety of space-sensitive laboratory locations, including incubators, benchtops, workstations, and the like. For instance, the spacing provides ventilation and thermal flow around the growth plates 100, for example during incubation and the like. As shown, each of the growth plates may include a top surface 102. The top surface 102 may include a front portion 130, a rear portion 132, and a side periphery of any dimension, sizes, orientations, and the like. Further, each of the growth plates 100 includes at least one well 120 that is generally recessed below the top surface 102. Other examples include two or more wells 120. In addition, at least one raised stacking surface 122 extends above the top surface 102. As shown, four raised stacking surfaces 122 are aligned at corners of the top surface 102. In particular examples, the raised stacking surfaces 122 are raised indentions, for instance as a result of molding or the like.

In some examples, the front portion 130 of the top surface includes a handling opening 126 for handling individual plates 100. For instance, the handling opening 126 may be indented toward the recessed well 120. As shown, the handling opening 126 is a rounded lip; however, other examples include similar geometrical shapes and configurations. As further shown, a pair of support ends 128 on opposite sides of the handling opening 126 may provide structural integrity of the plate, particularly during handling to support the weight of the plate and its contents.

Figure 7:
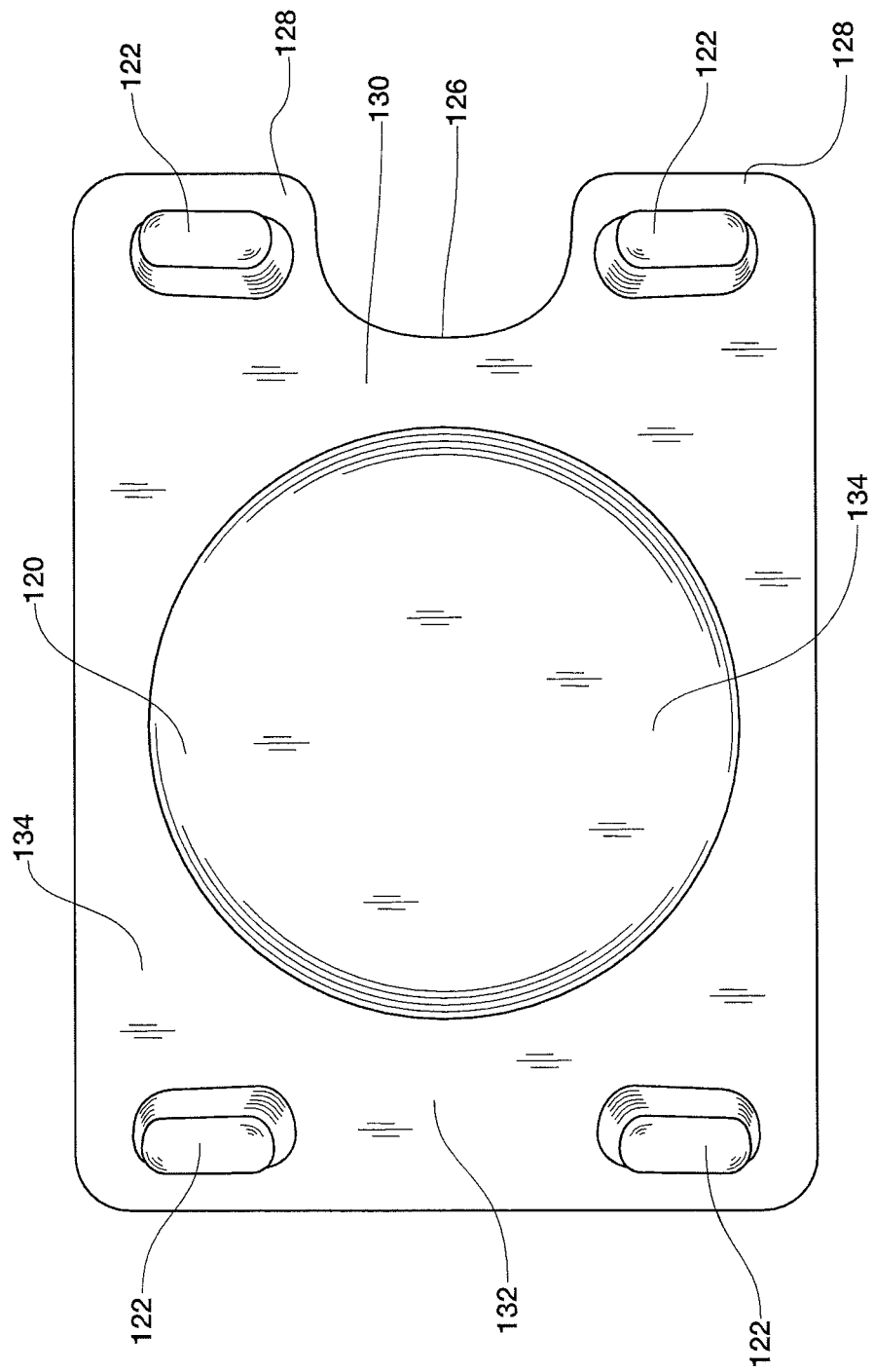
FIG. 7 is a top perspective view of one example of an isolated growth plate as introduced in FIG. 6.
Figure 8:
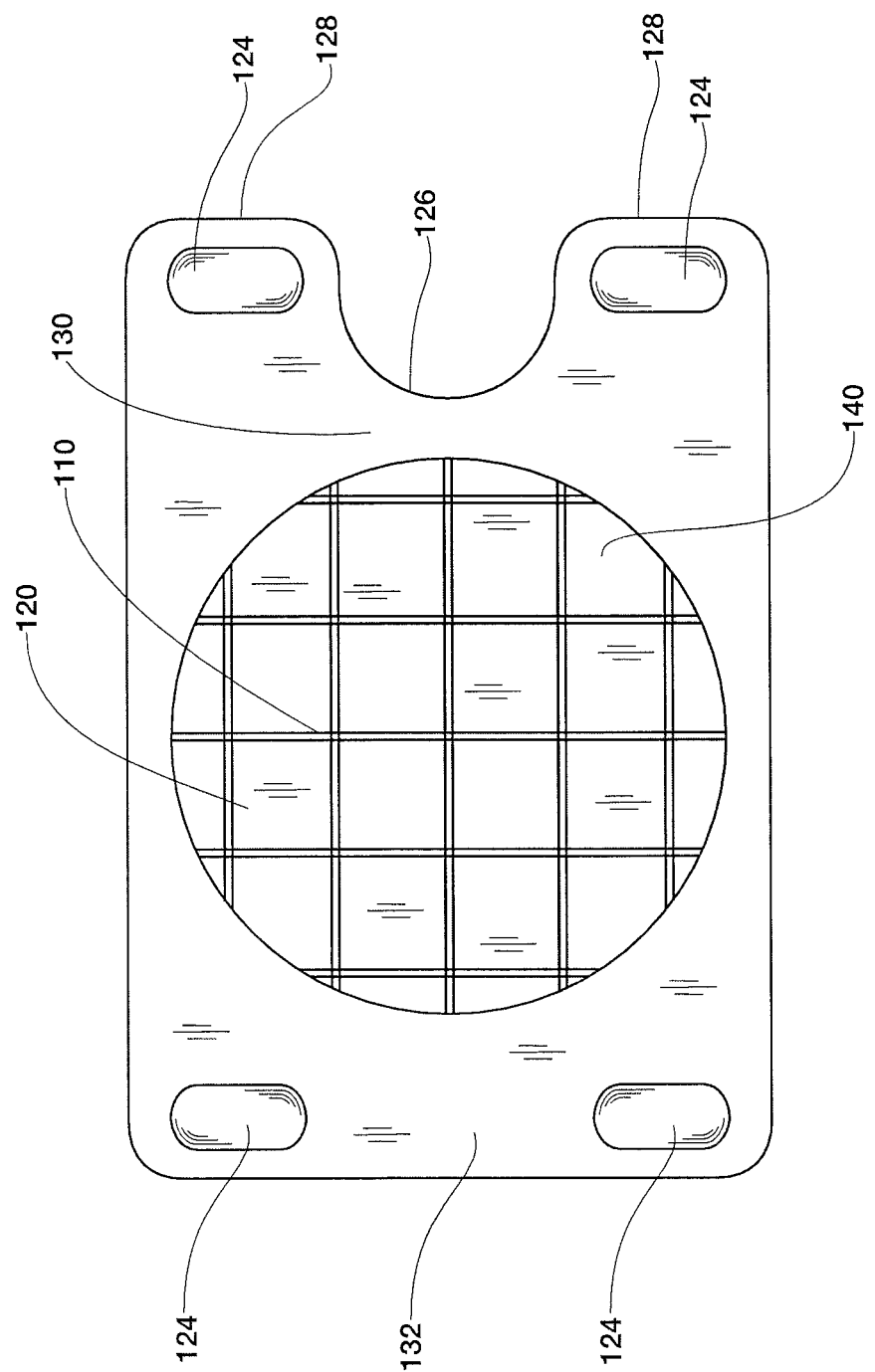
FIG. 8 is a bottom perspective view of one example of an isolated growth plate as introduced in FIG. 6.

As shown in the alternative embodiments in FIGS. 6-8, the raised stacking surfaces 122 may include tapered edges 136 to promote proper alignment of adjacent plates 100. The tapered edges 136 may aid in aligning adjacent plates, for instance guiding temporarily adjoining raised stacking surfaces 122 of one plate 100 with a receiving aperture 124 of a second opposing plate 100. Further, each of the plates 100 may include a grid 110 that is generally visible for colony counting as shown and described herein.

FIG. 8 shows one embodiment of the bottom the plate 100, wherein the recessed well 120 includes a bottom face 140. The bottom face 140 may be substantially flat for analyte testing as shown and described herein. The handling opening 126 may be handled with a user's finger, thumb, or the like to aid in positioning each individual plate 100. In addition, a receiving aperture 124 may be a hollow, or partially hollow, portion of the opposing raised stacking surfaces 122. Those of ordinary skill having the benefit of this disclosure will recognize additional receiving aperture 124 and raised stacking surfaces 122 geometry, orientations, and alignments.

Growth plate assembly embodiments, i.e. the stacked plates about one another as shown and described herein, include any number of individual plates. Certain growth plate assembly embodiments include about fifty growth plates; however, other examples include any number of growth plates for an intended use or testing sequence.

Any of the growth plate assemblies shown and described herein generally supports an upper growth plate 100 above the bottommost growth plate 100 on a surface, for instance an incubator surface, benchtop, or the like. However, in other exemplary examples, a rack or similar lower support may position the bottommost growth plate 100 above a surface.

Further examples of the growth plate assembly includes an identification feature to identify a particular testing batch of growth plates, sequence, status, or other laboratory technique.

Any of the growth plates shown and described herein may be any variety of culture devices. For instance, the growth plate may be a peel plate with a seal, for instance a peelable membrane. The growth plates may stacked in any of the assembled positions shown and described herein, wherein each plate includes media and the wells are sealed with seal. In use, the peel may be removed to add sample and then the seal is replaced. Further, as shown herein the plates may be incubated while stacked and sealed.

In particular examples, the growth plate can be a waterproof flat plate onto which a fibrous water-absorbent sheet may adheres may be formed from any waterproof material such as plastic or glass, but is preferably formed from transparent material so as to enable observation from the outside, including any of the printed grids shown and described herein. The growth plate can include a seal, cover or be in a clamshell-like configuration. The device can be made of polystyrene, glass, plastic, or similar material. In a clamshell configuration the device can be made from PVC or other flexible plastic material such as PET, or polyethylene. Regardless of the device configuration, upon drying of the slurry an in-situ created, media-infused papercloth-like matrix can be formed as generally shown and described in U.S. Provisional Patent Application No. 61/701,123, filed Sep. 14, 2012, and U.S. Provisional Patent Application No. 61/738,153, filed Dec. 17, 2012, the teachings of which are hereby incorporated by reference in their entireties.

Figure 9:
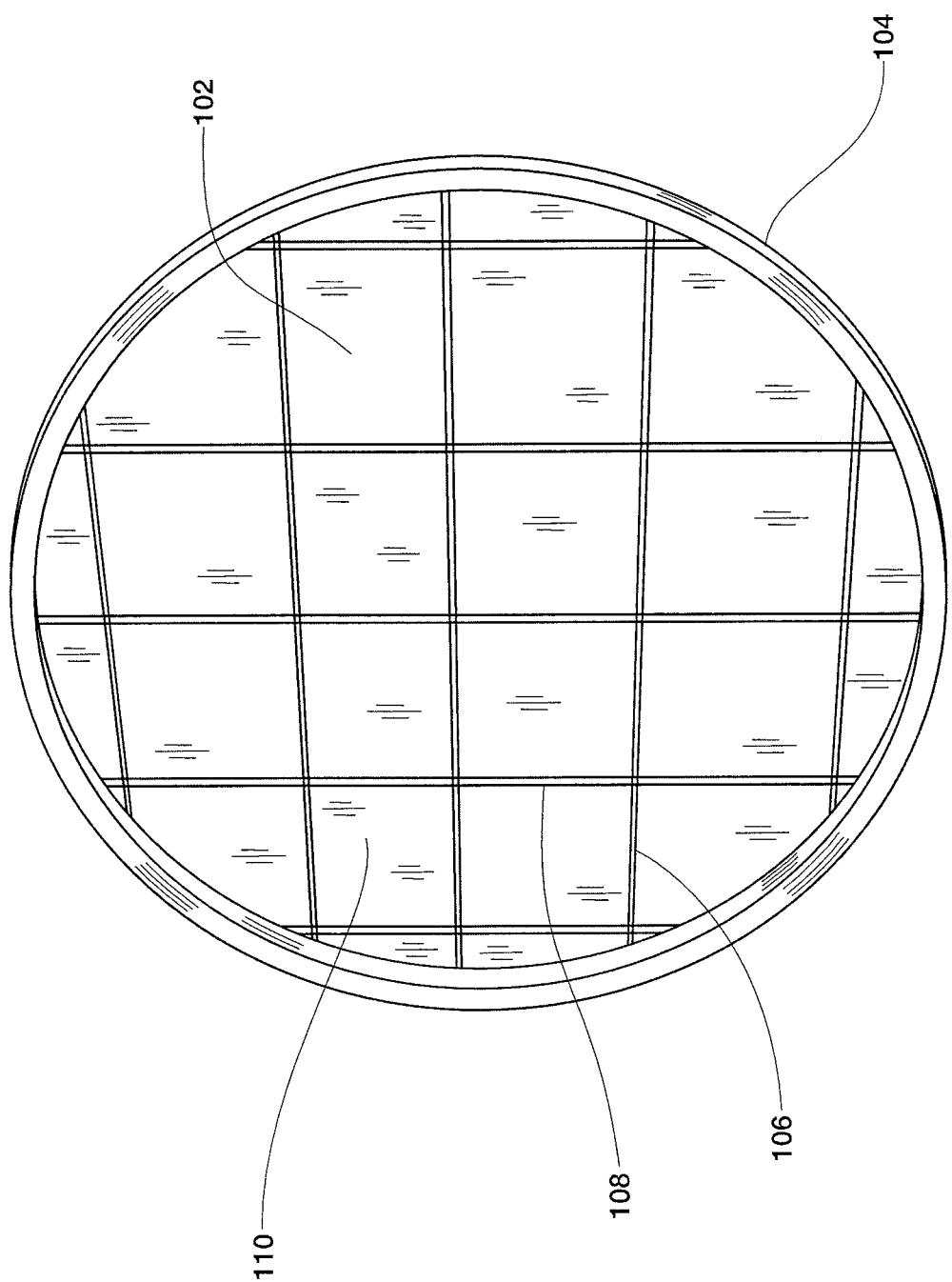
FIG. 9 is a top view of one embodiment of a well of an isolated growth plate.

As further shown in FIG. 9, any of the growth plates and/or plate media devices or similar packaging described herein, may include a grid 110. The grid 110 may have a horizontal 108 and/or vertical 106 component useful for colony counting. In particular examples, the grid 110 is molded, printed, or the like on the rear surface 104. The grid 110 may be printed in a variety of ways, including inkjet printing, pad printing and the like. Regardless of the grid type, the grid 110 is visible through the generally transparent culture device to the front surface 102. In particular examples, the grid 110 is visible front the front surface 102 for colony counting after any of the tests described herein have been developed.

Additional embodiments include growth plate assemblies, kits, and packaging systems. The kits may include one or more of the following: a growth plate assembly, i.e. any of the assembly elements as shown and described herein; a positioning pad, a plurality of growth plates, i.e. any of the plates shown and described herein; and a resalable enclosure.

One example of the kits includes a positioning pad that serves as a temporary holding device on a benchtop, workstation, or similar laboratory surface to hold any of the growth plates shown and described herein. For instance, the positioning pad may have a bottom adhesive that is generally adapted to removably secure the pad to a surface without leaving a reside on the surface. The surface may include epoxy resin, solid phenolic, stainless steel, plastic laminate, or any other surface or countertop. Similarly, the positioning pad may have an upper adhesive that is generally adapted to removably secure a rear surface the growth plate to the positioning pad. As shown and described above, the growth plate may include seal, and the positioning pad thus is used to temporarily secure the growth plate in a fixed position when the seal is lifted and during any testing step or sequence.

In particular examples, the adhesive on the positioning pad 12 has a tack of about 100 to about 700 grams per square centimeter, for instance a tack of about 400 to about 550 grams per square centimeter. Further, the adhesive pad may have an initial peel of about 15 to about 75 ounces per inch, for instance an initial peel of about 25 to about 55 ounces per inch. The adhesive pad may have an ultimate peel of about 15 to about 95 ounces per inch, for instance an ultimate peel of about 55 to about 75 ounces per inch.

As shown in FIG. 10, a kit may include an enclosure 14 for retaining any of the elements shown and described herein. The enclosure 14 may include a moisture barrier 54 to provide a sufficient barrier against moisture for the elements within the enclosure, particularly during packaging, shipment, storage, and the like. For instance, one example of the enclosure 14 provides a moisture vapor transmission rate (MVTR) of about 48 ga PET/25μ EXPE/ 6μ FOIL/ADH/90μ LLDPE. The thickness of the enclosure 14 may be about 5 millimeters, while other examples include additional thicknesses and layers. Any of the enclosures 14 shown and described herein may be resealable. In some examples, the enclosure is a resealable bag. In particular examples, the resealable enclosure 14 is sized to hold at least fifty growth plates 100; however, those of ordinary skill in the art having the benefit of this disclosure will recognize a variety of other enclosures and kits.

Numerous characteristics and advantages have been set forth in the foregoing description, together with details of structure and function. Many of the novel features are pointed out in the appended claims. The disclosure, however, is illustrative only, and changes may be made in detail, especially in matters of shape, size, and arrangement of parts, within the principle of the disclosure, to the full extent indicated by the broad general meaning of the terms in which the general claims are expressed. It is further noted that, as used in this application, the singular forms "a," "an," and "the" include plural referents unless expressly and unequivocally limited to one referent.

We claim:

1. A growth plate for receiving a sample, said growth plate comprising:
   a. an upper face having a front portion, a rear portion, and a side periphery;
   b. a recessed well having a sunken wall protruding below said upper face;
   c. a pair of opposing proximate extensions arranged on opposing proximate tabs and said opposing proximate extensions being offset from said recessed well and extending above said upper face and spaced apart from one another to define an access indent, wherein at least one of said opposing proximate extensions comprises an underside receiving aperture;
   d. a distal raised platform adjacent said recessed well and extending above said upper face, and wherein said distal raised platform having an underside cavity and a width adapted to support a width of a user's finger; and
   e. a removable peel layer having a peel tab, wherein said removable peel layer encloses said recessed well and at least a portion of said upper face in an unopened position and subsequently encloses said recessed well and at least a portion of said upper face after receiving said sample, and wherein said recessed well positioned between said distal raised platform and said opposing proximate extensions, and wherein said recessed well aligned below and spaced from said distal raised platform on said upper face, wherein said distal raised platform extends above a horizontal plane defined by said upper face, and wherein said horizontal plane is parallel to a lower horizontal plane defined by a bottom wall of the said recessed well.

2. The growth plate of claim 1, wherein said distal raised platform being rectangular and spanning a length of a diameter of said recessed well.

3. The growth plate of claim 1, wherein said front portion includes a handling opening defined by said access indent.

4. The growth plate of claim 1, wherein said opposing proximate extensions include tapered edges configured to guide adjoining opposing proximate extensions and a corresponding receiving aperture in an assembled stacked position.

5. The growth plate of claim 1, wherein said recessed well includes a grid.

6. The growth plate of claim 1, wherein said recessed well includes a grid visible for colony counting.

7. The growth plate of claim 1, wherein said growth plate is a peel plate wherein said removable peel layer is configured to temporarily enclose said recessed well and at least a portion of said upper face.

8. The growth plate of claim 7, wherein said peel tab of said removable peel layer removably secured to a front end of said growth plate.

9. The growth plate of claim 7, wherein said removable peel layer includes a self-wicking adhesive periphery configured to removably adhere to said upper face of said growth plate.

10. A growth plate assembly comprising:
    a. a plurality of growth plates, wherein each of said plurality of growth plates having
       i. a recessed well protruding below an upper face of said growth plate;
       ii. a raised platform on a first end of said growth plate adjacent to said recessed well, said raised platform having an underside cavity and a width adapted to support a width of a user's finger; and
       iii. a pair of opposing proximate extensions extending from a second end of said growth plate and offset from said recessed well and separated by an access indent, each of said opposing proximate extensions having an underside receiving aperture, and
    wherein a first growth plate's raised platform and extended proximate extensions are configured to be received by a second growth plate's corresponding underside cavity of raised platform and underside receiving aperture of opposing proximate extensions in an aligned position, thereby said first growth plate being removably secured about said second growth plate.

11. The growth plate assembly of claim 10, wherein a third growth plate's raised platform and proximate extensions are received by said second growth plate's corresponding platform cavity and receiving aperture in an aligned position, thereby said first, second, and third growth plate being removably secured about one another.

12. The growth plate assembly of claim 10, wherein each of said growth plates being sterilized and including a removable peel layer.

13. The growth plate assembly of claim 12, wherein said removable peel layer includes a peel tab.

14. A growth plate for receiving a sample, said growth plate comprising:
   a. a recessed well having a sunken wall protruding below an upper face of said growth plate;
   b. a pair of opposing proximate extensions arranged on opposing proximate tabs, and said opposing proximate extensions being offset from said recessed well and extending above said upper face and spaced apart from one another, wherein each of said opposing proximate extensions having an underside receiving aperture;
   c. a handling opening between said opposing proximate extensions having a peel tab of a removable peel layer aligned on said handling opening, wherein said removable peel layer encloses said recessed well and at least a portion of said upper face in an unopened position and subsequently encloses said recessed well and at least a portion of said upper face after receiving said sample; and
   d. a distal raised platform having a width adapted to support a width of a user's finger and being adjacent said recessed well and extending above said upper face, wherein said raised platform having an underside cavity, and wherein said distal raised platform extends above a horizontal plane defined by said upper face, and wherein said horizontal plane is parallel to a lower horizontal plane defined by a bottom wall of the said recessed well.

* * * * *